US009803492B2

(12) United States Patent
Ruhge et al.

(10) Patent No.: US 9,803,492 B2
(45) Date of Patent: *Oct. 31, 2017

(54) OPTICAL MEASUREMENT SYSTEM FOR DETECTING TURBINE BLADE LOCKUP

(71) Applicant: Siemens Energy, Inc., Orlando, FL (US)

(72) Inventors: Forrest R. Ruhge, Orlando, FL (US); Clifford Hatcher, Jr., Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 273 days.

This patent is subject to a terminal disclaimer.

(21) Appl. No.: 14/576,919

(22) Filed: Dec. 19, 2014

(65) Prior Publication Data

US 2016/0177776 A1    Jun. 23, 2016

(51) Int. Cl.
*F01D 11/00* (2006.01)
*F01D 5/22* (2006.01)
(Continued)

(52) U.S. Cl.
CPC ............. *F01D 11/006* (2013.01); *F01D 5/22* (2013.01); *F01D 5/12* (2013.01); *F01D 5/30* (2013.01);
(Continued)

(58) Field of Classification Search
CPC ........ F01D 21/003; F01D 5/005; F01D 11/20; F01D 17/02; F01D 11/14; F01D 17/20; F01D 21/04; F01D 25/285; F01D 21/14; F01D 5/22; F01D 5/26; F01D 5/30; F01D 11/006; F05D 2260/80; F05D 2260/83; F05D 2270/804; F05D 2270/8041; F05D 2220/36; F05D 2270/80; F05D 2220/74; F03D 17/00; G01H 9/00; G01H 9/004; G06T 2207/30164; G06T 7/0004; G06T 2207/10016; G06T 7/001; G06T 2207/10152; G06T 2207/30108; G06T 7/0022; G06T 7/20; G01B 11/14;
(Continued)

(56) References Cited

U.S. PATENT DOCUMENTS

4,572,663 A * 2/1986 Greene ................. F01D 21/003
                                                                348/132
5,095,252 A * 3/1992 Kurth ..................... H05B 41/34
                                                                315/200 A
(Continued)

*Primary Examiner* — Peter Macchiarolo
*Assistant Examiner* — Timothy Graves (57) ABSTRACT

An optical measurement system for detecting at least one locked blade assembly in a gas turbine. The system includes at least one light source for emitting light that impinges on a blade surface of each blade in a row of blade assemblies. The system also includes a video device for imaging the blades as the blades rotate about the center axis. Further, the system includes a controller for controlling operation of the light source and video device. The controller detects a pixel intensity associated with each blade and a spacing between each pixel intensity wherein a change in spacing between consecutive pixel intensities indicates that a distance between consecutive blades has changed relative to the first distance thereby indicating at least one locked blade assembly.

20 Claims, 6 Drawing Sheets

(51) Int. Cl.
    *G01M 1/00*     (2006.01)
    *F01D 5/30*     (2006.01)
    *F01D 5/12*     (2006.01)
    *G01N 21/88*    (2006.01)
    *F01D 21/00*    (2006.01)
    *G01N 21/954*   (2006.01)
    *F01D 25/34*    (2006.01)

(52) U.S. Cl.
    CPC ............ *F01D 21/003* (2013.01); *F01D 25/34* (2013.01); *F05D 2220/32* (2013.01); *F05D 2260/80* (2013.01); *F05D 2260/83* (2013.01); *G01M 1/00* (2013.01); *G01N 21/88* (2013.01); *G01N 2021/9546* (2013.01)

(58) Field of Classification Search
    CPC . G01B 7/14; G01B 9/02; G01B 11/00; G01B 11/022; G01M 15/14; G01M 11/081; G01M 1/00; F05B 2270/8041; F05B 2270/804; F05B 2240/30; G01J 5/08; G01J 5/0896; G02B 23/2484; G02B 21/367; G01C 25/00
    USPC ................ 73/660, 112.01, 147, 655; 416/61; 356/614, 138, 152.1; 415/118
    See application file for complete search history.

(56) References Cited

U.S. PATENT DOCUMENTS

| | | | |
|---|---|---|---|
| 6,992,315 B2* | 1/2006 | Twerdochlib | F01D 5/005 250/330 |
| 7,619,728 B2* | 11/2009 | Ogburn | G02B 23/2484 250/208.1 |
| 2007/0132461 A1* | 6/2007 | Holmquist | F01D 17/02 324/644 |
| 2013/0115050 A1* | 5/2013 | Twerdochlib | F01D 21/14 415/118 |

* cited by examiner

OPTICAL MEASUREMENT SYSTEM FOR DETECTING TURBINE BLADE LOCKUP

CROSS-REFERENCE TO RELATED APPLICATION

The entire disclosure of U.S. application Ser. No. 14/576,747, filed on the same day herewith, entitled LASER MEASUREMENT SYSTEM FOR DETECTING TURBINE BLADE LOCKUP and having inventors Clifford Hatcher, Jr. and Forrest R. Ruhge, is incorporated by reference in its entirety.

FIELD OF THE INVENTION

This invention relates to the detection of locked blade assemblies in a gas turbine, and more particularly, to an optical measurement system that includes at least one light source for emitting light that impinges on a blade surface of each blade in a row of blades of the gas turbine, at least one video device for capturing images of the blades as the blades rotate about the center axis and a controller for detecting a pixel intensity associated with each blade and a spacing between each pixel intensity wherein a change in spacing between consecutive pixel intensities indicates that a distance between consecutive blades has changed relative to a first distance thereby indicating at least one locked blade assembly.

BACKGROUND OF THE INVENTION

Figure 1:
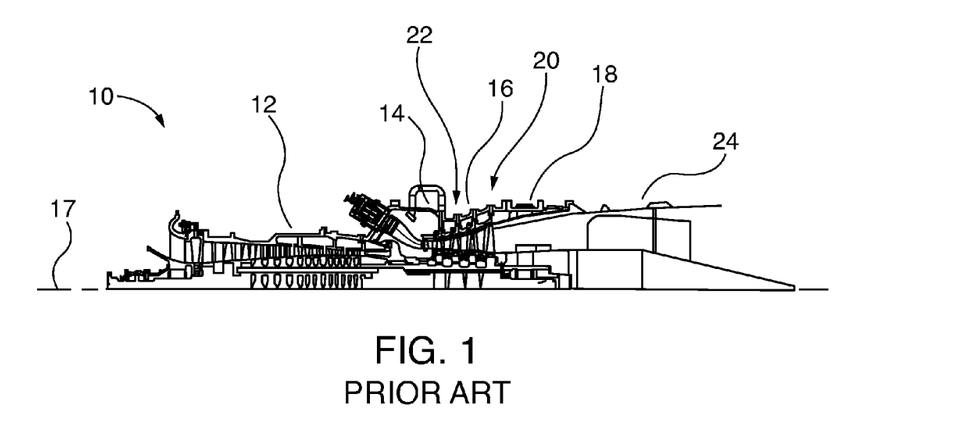
FIG. 1 is a partial view an axial flow gas turbine.

In various multistage turbomachines used for energy conversion, such as gas turbines, a fluid is used to produce rotational motion. Referring to FIG. 1, an axial flow gas turbine 10 includes a compressor section 12, a combustion section 14 and a turbine section 16 arranged along a horizontal center axis 17. The compressor section 14 provides a compressed air flow to the combustion section 14 where the air is mixed with a fuel, such as natural gas, and ignited to create a hot working gas. The turbine section 16 includes a plurality of blade assemblies 20 arranged in a plurality of rows. The hot gas expands through the turbine section 16 where it is directed across the rows of blade assemblies 20 by associated stationary vanes 22. The blade assemblies 20 are ultimately attached to a shaft that is rotatable about the center axis 17. As the hot gas passes through the turbine section 16, it causes the blade assemblies 20 and thus the shaft to rotate, thereby providing mechanical work. Each row of blade assemblies 20 and associated vanes 22 than a stage. In particular, the turbine section 16 may include four rows of blade assemblies 20 and associated vanes 22 to form four stages. The gas turbine 10 further includes an exhaust cylinder section 18 located adjacent the turbine section 16 and an outer diffuser section 24 located adjacent the exhaust cylinder section 18.

Figure 2:
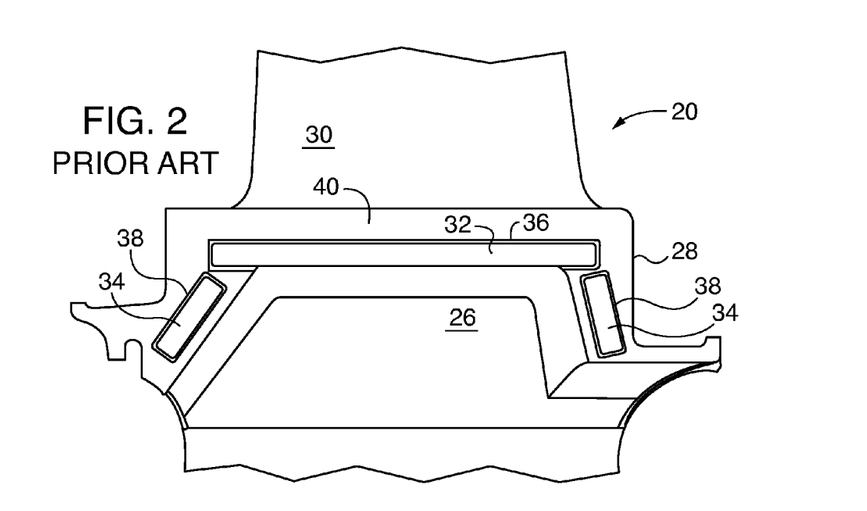
FIG. 2 is a view of an exemplary rotatable blade assembly used in the gas turbine.

Many gas turbines may utilize a portion of the compressed air generated by the compressor section 12 as a cooling fluid for cooling hot components of the combustion 14 and turbine sections 16 of the gas turbine 10. In one type of cooling system design known as a closed loop cooling system, a seal pin arrangement is used to form a seal between adjacent rotating blade assemblies 20. FIG. 2 illustrates an exemplary rotatable blade assembly 20 used in the gas turbine 10. Blade assembly 20 includes a root section 26 that is attached to a rotor and a platform section 28 that extends from the root section 26. An airfoil or turbine blade 30 extends from the platform 28 on an opposite side from the root section 26. The platforms 28 are located on the rotor such that each blade 30 is substantially evenly spaced from an adjacent blade 30. The blade 30 extracts heat and pressure energy from the hot gas as it passes over the blade assembly 20 and converts the energy into mechanical energy by rotating the shaft.

The platform 28 is sealed and damped against a corresponding platform 28 of an adjoining blade assembly 20 by seal pins 32 and 34. The pins 32 and 34 are positioned in corresponding pin slots 36 and 38 formed into a surface 40 of the platform 28. The pin slots 36 and 38 are arranged such that centrifugal force generated by rotation about the center axis 17 loads the pins 32 and 34. This forces the pins 32 and 34 out of a resting position in the pin slots 36 and 38 so that the pins 32 and 34 are urged against a corresponding surface of a platform 28 of an adjoining blade assembly 20, thereby forming a seal and damping structure.

SUMMARY OF INVENTION

An optical measurement system for detecting at least one locked blade assembly in a gas turbine is disclosed. The system includes at least one light source for emitting light that impinges on a blade surface of each blade in a row of blade assemblies. The system also includes a video device for imaging the blades as the blades rotate about the center axis. Further, the system includes a controller for controlling operation of the light source and video device. The controller also detects a pixel intensity associated with each blade and a spacing between each pixel intensity wherein a change in spacing between consecutive pixel intensities indicates that a distance between consecutive blades has changed relative to a first distance thereby indicating at least one locked blade assembly.

Further, a method is disclosed for detecting at least one locked blade assembly in a gas turbine having a plurality of blade assemblies arranged in rows about a center axis wherein each blade assembly includes a blade and wherein adjacent blades in a row are separated by a first distance forming a space between adjacent blades. The method includes emitting light that impinges on a blade surface of each blade in a row of blades and imaging the blades as the blades rotate about the center axis. The method also includes detecting a pixel intensity for each blade and a spacing between each pixel intensity. In particular, a change in spacing between consecutive pixel intensities relative to other pixel intensities indicates that a distance between consecutive blades has changed relative to the first distance thereby indicating at least one locked blade assembly.

Those skilled in the art may apply the respective features of the present disclosure jointly or severally in any combination or sub-combination.

BRIEF DESCRIPTION OF DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected." "supported," and "coupled" and variations thereof are used broadly and encompass direct and indirect mountings, connections, supports, and couplings. Further, "connected" and "coupled" are not restricted to physical or mechanical connections or couplings.

It has been found by the inventors herein that at least one seal pin 32, 34 associated with at least one blade assembly 20 of the turbine section 16 may migrate from an associated pin slot 36, 38 and become undesirably wedged between adjoining or consecutive platforms 28. Pin migration may occur during a known turning gear operation wherein a turning gear mechanism is used to slowly rotate a turbine shaft prior to startup of a cold gas turbine 10 or after shutdown of the gas turbine 10 to remove or inhibit sagging of the shaft. During a turning gear operation, the shaft rotates at a turning gear speed (for example, approximately 3 to 5 rpm) that is substantially less than normal turbine operating speed (for example, approximately 3600 rpm). This results in the generation of a substantially reduced centrifugal force that in turn sufficiently unloads the seal pins 32, 34 such that at least one pin 32, 34 becomes loose, migrates out of its associated slot 36, 38 and ultimately becomes wedged in between adjoining platforms 28. When a seal pin 32, 34 is wedged between adjoining platforms 28, an operational frequency and/or vibration characteristic of the blade 30 is changed that results in an undesirable increase in mechanical stress exerted on the blade 30 at a location near the platform 28.

The unloading of the pins 32, 34 due to reduced rotational speed during a turning gear operation also results in each blade assembly 20 being loosely attached to its corresponding rotor. As a result, each blade assembly 20 is able to shift or move as it is rotated about the center axis 17. When a pin 32, 34 becomes wedged between adjoining platforms 28, movement of the adjoining blade assemblies 20 is inhibited and the adjoining blade assemblies 20 become immobilized, i.e. the blades assemblies 20 are locked. Further, the wedged pin 32, 34 displaces the adjoining platforms 28 away from each other such that a distance between corresponding consecutive locked blades 30 is increased, thus resulting in unevenly spaced blades 30 in a row of blades 30. Further, displacement of the adjoining platforms 28 away from each other also decreases the distance between a locked blade 30 and an adjacent unlocked blade 30.

Figure 3:
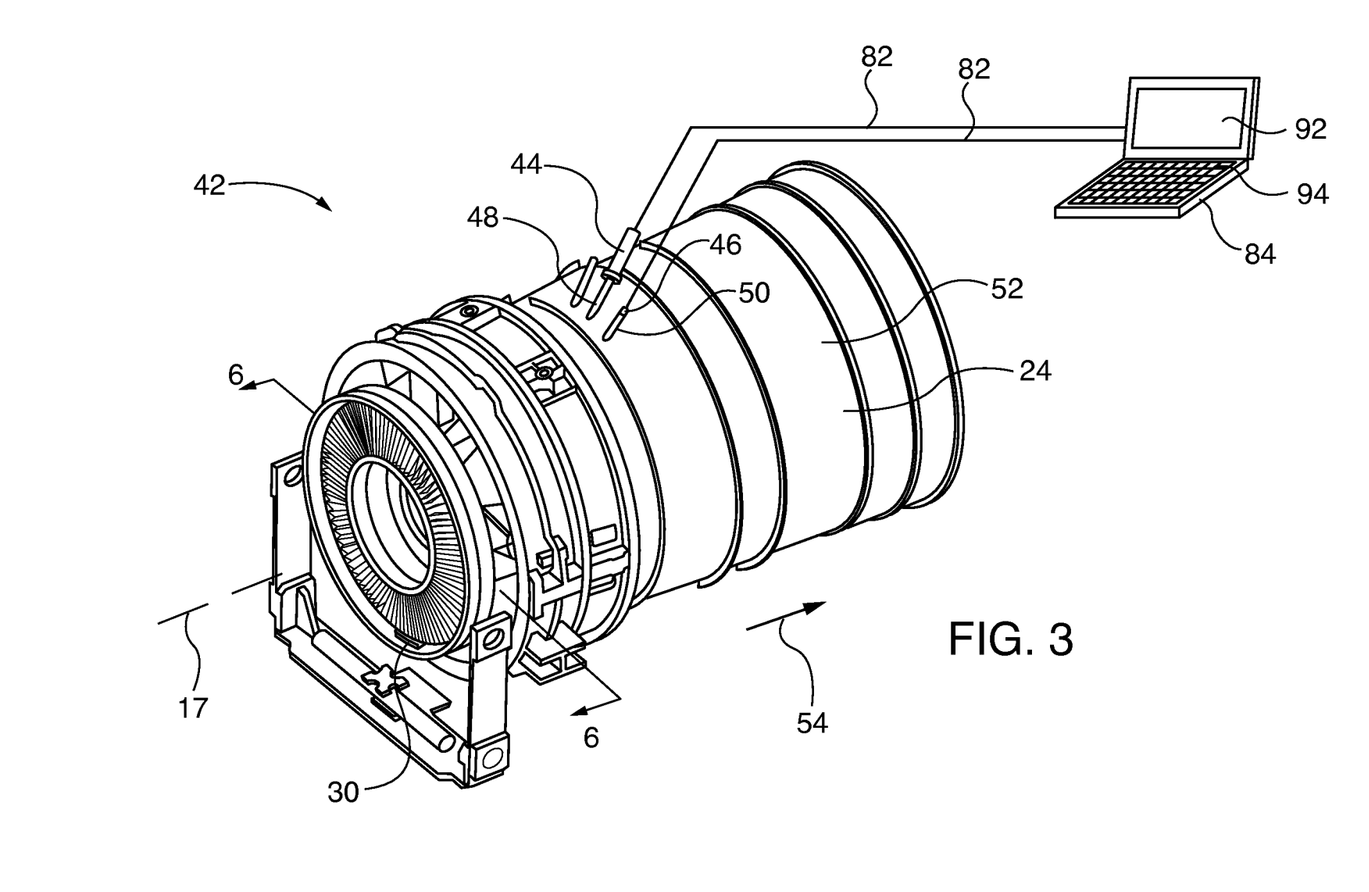
FIG. 3 is a schematic of an optical measurement system for detection of blade lockup of consecutive blade assemblies.
Figure 4:
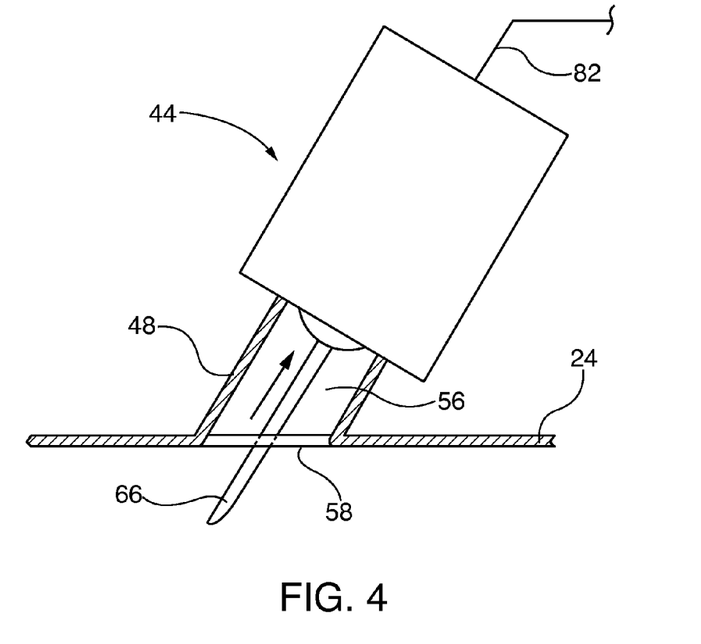
FIG. 4 is a partial cross sectional view of a video port shown in FIG. 3.
Figure 5:
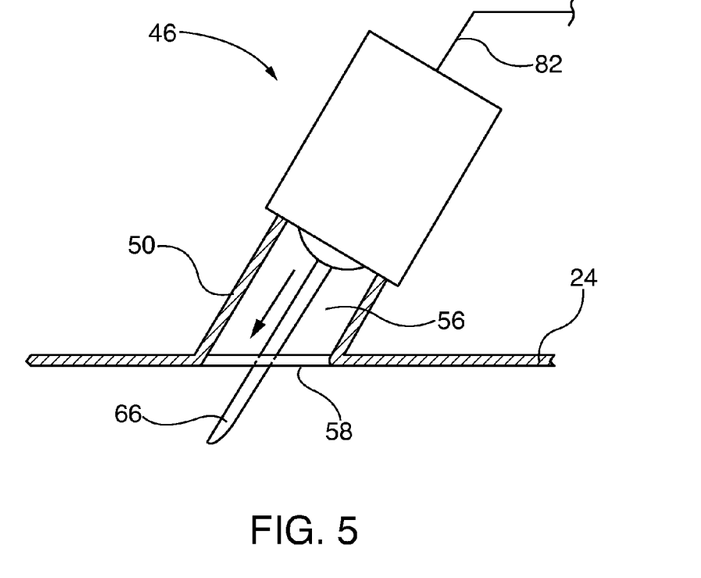
FIG. 5 is a partial cross sectional view of a light port shown in FIG. 3.

Referring to FIG. 3, an optical measurement system 42 for detection of blade lockup is shown. Although the current disclosure discusses blade lockup in a gas turbine, it is understood that the current disclosure is applicable to other types of turbine engines that experience blade lockup. The system 42 includes a known video camera 44 and light source 46. In an alternate embodiment, the camera 44 and light source 46 may be combined to form a video module. The camera 44 and light source 46 are attached to angled video 48 and light 50 ports, respectively. The video 48 and light 50 ports may be located on a surface 52 of the gas turbine such as the outer diffuser 24, although it is understood that other surface locations may be used. Arrow 54 depicts a direction of exhaust flow in the outer diffuser 24. FIGS. 4 and 5 depict partial cross sectional views of the video 48 and light 50 ports, respectively. The ports 48, 50 may be preexisting ports or new ports formed in the outer diffuser 24. The ports 48, 50 each include a through hole 56 and a lens 58 fabricated from sapphire glass that forms part of the outer diffuser 24. In an alternate embodiment, a plurality of cameras 44, light sources 46 and associated video 48 and light 50 ports may be used. For example, the cameras 44, light sources 46 and associated video 48 and light 50 ports may be located in a circumferential and/or staggered arrangement around the outer diffuser 24.

Figure 6:
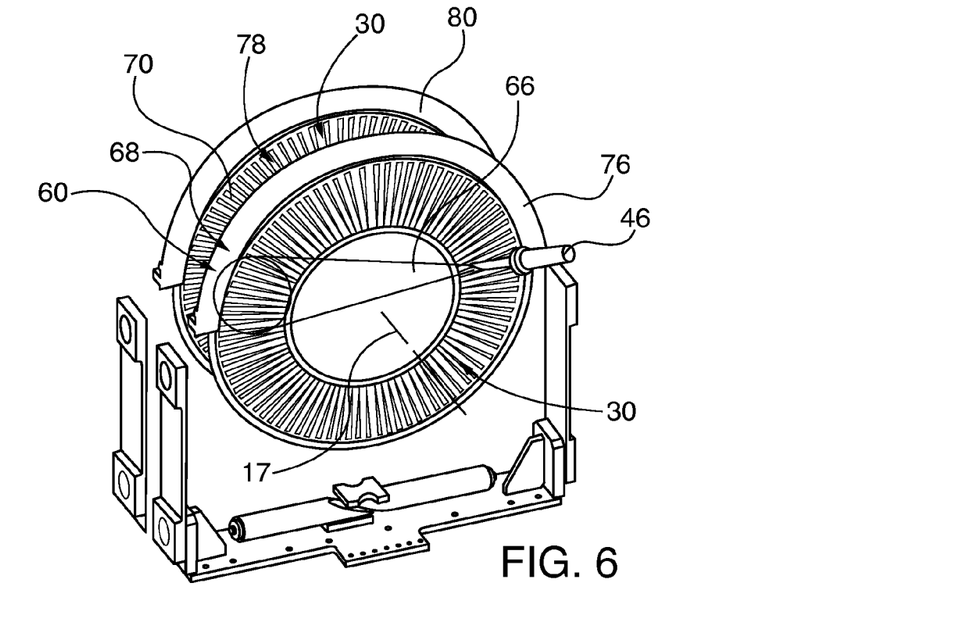
FIG. 6 is a view of a row of blades along view line 6-6 of FIG. 3.
Figure 7:
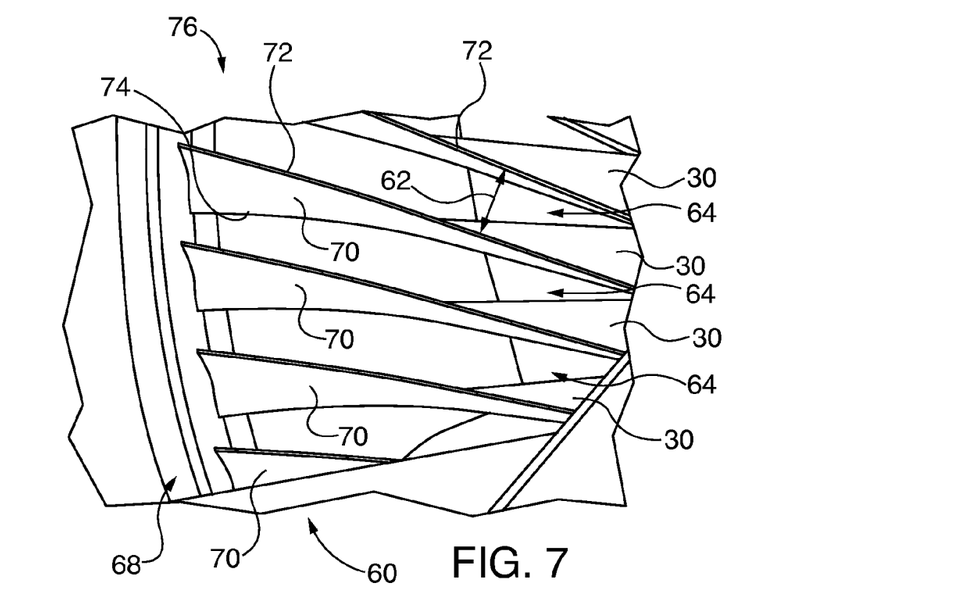
FIG. 7 is an enlarged view of a section of FIG. 6.

Referring to FIG. 6, a view of a row of blades 30 along view line 6-6 of FIG. 3 is shown. Referring to FIG. 7, an enlarged view of section 60 of FIG. 6 is shown. When adjoining blade assemblies 20 are not locked (i.e. when pins 32, 34 are not wedged between adjoining platforms 28), a trailing edge 72 of each blade 30 is separated by a first distance 62 from a trailing edge 72 of an adjacent blade 30 thereby forming an evenly spaced blade arrangement wherein each blade 30 is separated from an adjacent blade 30 by a space 64. Referring to FIGS. 4-7, the light source 46 emits light 66 that is transmitted through the hole 56 and lens 58 and impinges on a section 68 of the gas turbine 10 that includes a row of blades 30, thereby forming an illuminated section 68. The light source 46 provides a light output sufficient for capturing video images of the blades 30. In an embodiment, the light output of the light source is approximately 1000 lumens.

The light 66 impinges on a blade surface 70 of each blade 30 as the blades 30 move in and out of the illuminated section 68 during rotation of the blades 30 about the center axis 17. For example, the light 66 impinges on a blade surface 70 extending between the trailing edge 72 and a leading edge 74 of each blade 30. The light 66 is then reflected from each blade surface 70 and is transmitted through the lens 58 and hole 56 to ultimately impinge on the camera 44. The camera 44 captures images of the blades 30 as the blades 30 move through the illuminated section 68. In an embodiment, the video 48 and light 50 ports are oriented such that images are captured of a row of blades 30 located adjacent the exhaust cylinder section 18, such as a fourth row 76 of blades 30 of a four stage turbine section 16. It is understood that the camera 44 and light source 46 may be oriented such that images of other rows of blades 30 of the turbine section 16 are captured.

The light 66 is also transmitted through the spaces 64 between the blades 30 and impinges on internal surfaces 78 of the gas turbine 10 that are located behind the blades 30 of the fourth row 76 and correspond to the spaces 64. By way of example, the internal surfaces 78 may be a blade surface 70 of at least one blade 30 located in a row 80 of blades 30 adjacent to the fourth row 76 of blades 30 and/or its associated components. A blade surface 70, such as the trailing edge 72, of a blade 30 in the fourth row 76 is located closer to the camera 44 and light source 46 than other portions of the same blade 30, such as the leading edge 74 and, further, than the blades 30 in the adjacent row 80. Thus, an amount of light reflected from the trailing edge 72 is substantially greater than an amount of light reflected from other portions of the blade 30 and the blades 30 in the adjacent row 80.

Referring back to FIG. 3, the system 42 also includes a computer 84 coupled to the camera 44 and light source 46 using a known technique such as a fiber optic cable 82 or alternatively a known wireless technique may be used. The system 42 determines a pixel intensity of the light reflected from the illuminated section 68. In particular, light reflected from the trailing edge 72 of each blade 30 causes the formation of an associated peak pixel intensity. This forms a plurality of spaced apart peak pixel intensities as the blades 30 are rotated about the center axis 17. As previously described, a locked blade assembly 20 increases the distance between corresponding consecutive locked blades 30 to a distance greater than the first distance 62. Thus, a change in the spacing between consecutive peaks of pixel intensity is indicative of a change in the distance between consecutive blades 30, thereby indicating a locked blade assembly 20.

Figure 8:
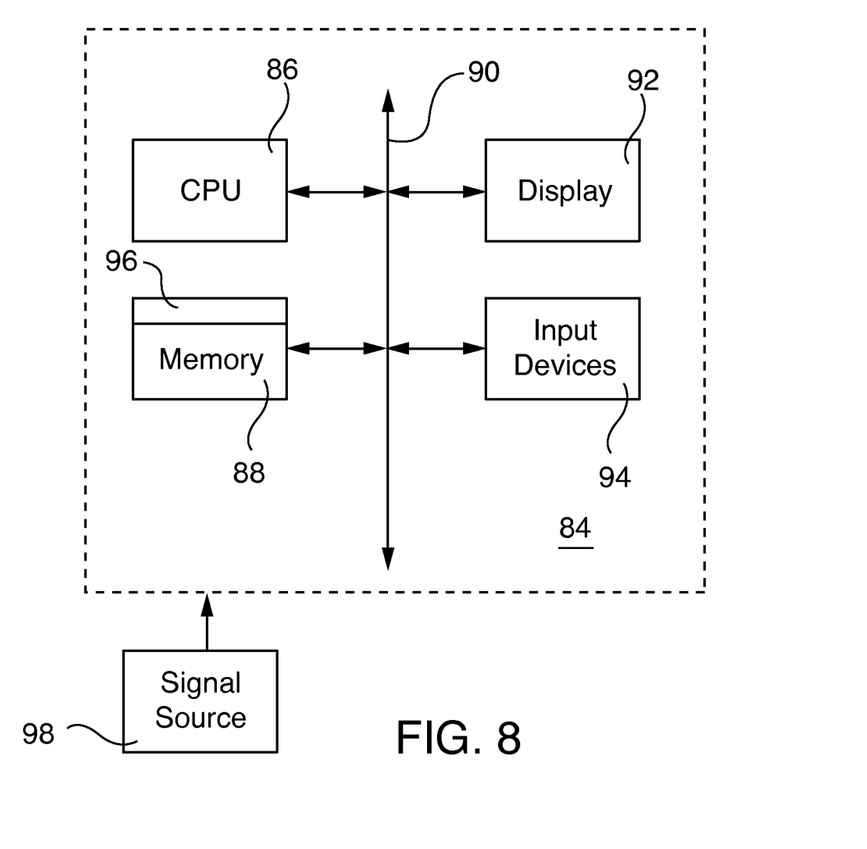
FIG. 8 is a block diagram of a computer.

The computer 84 includes software and drivers that enable the computer 84 to serve as controller for controlling operation of the laser device 44 and photon detector 46 and to process, visualize and store measurement data. The computer 84 may use well-known computer processors, memory units, storage devices, computer software, and other components. A high level block diagram of such a computer 84 is illustrated in FIG. 8. Computer 84 may include a central processing unit (CPU) 86, a memory 88 and an input/output (I/O) interface 90. The computer 84 is generally coupled through the I/O interface 90 to a display 92 for visualization and various input devices 94 that enable user interaction with the computer 84 such as a keyboard, keypad, touchpad, touchscreen, mouse, speakers, buttons or any combination thereof. Support circuits may include circuits such as cache, power supplies, clock circuits, and a communications bus. The memory 88 may include random access memory (RAM), read only memory (ROM), disk drive, tape drive, etc., or a combination thereof. Embodiments of the present invention may be implemented as a routine 96 that is stored in memory 88 and executed by the CPU 88 to process the signal from a signal source 98. As such, the computer 84 is a general purpose computer system that becomes a specific purpose computer system when executing the routine 96. The computer 84 can communicate with one or more networks such as a local area network (LAN), a general wide area network (WAN), and/or a public network (e.g., the Internet) via a network adapter. One skilled in the art will recognize that an implementation of an actual computer could contain other components as well, and that FIG. 8 is a high level representation of some of the components of such a computer for illustrative purposes.

The computer 84 also includes an operating system and micro-instruction code. The various processes and functions described herein may either be part of the micro-instruction code or part of the application program (or a combination thereof) which is executed via the operating system. In addition, various other peripheral devices may be connected to the computer platform such as an additional data storage device and a printing device. Examples of well-known computing systems, environments, and/or configurations that may be suitable for use with computer 88 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

It is to be understood that exemplary embodiments of the present invention may be implemented in various forms of hardware, software, firmware, special purpose processors, or a combination thereof. In one embodiment, aspects of the current disclosure may be implemented in software as an application program tangibly embodied on a computer readable storage medium or computer program product. As such, the application program is embodied on a non-transitory tangible media. The application program may be uploaded to, and executed by, a processor comprising any suitable architecture.

Test Results

Figure 9:
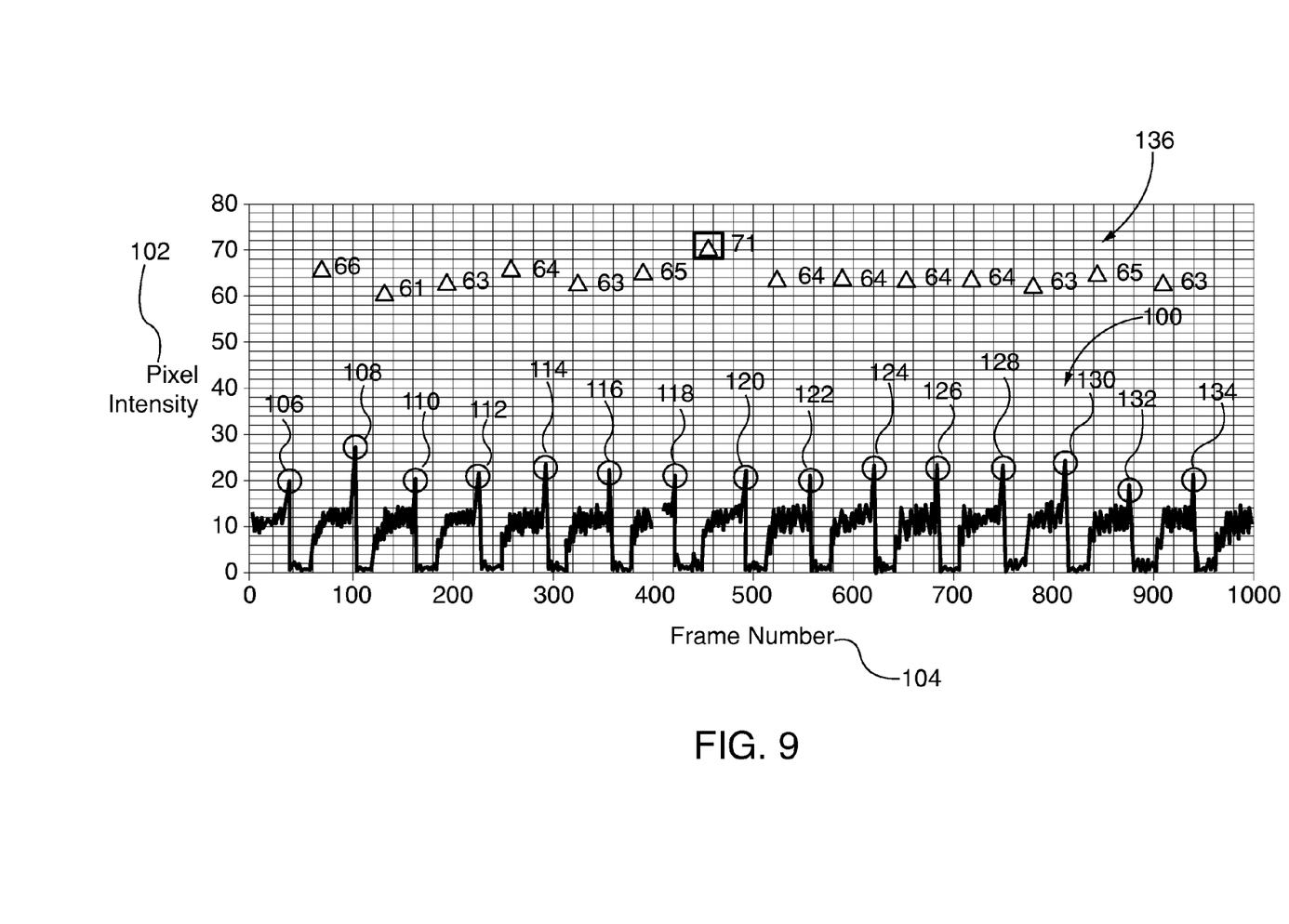
FIG. 9 is a graph of test results in which as pixel intensity of the light reflected from an illuminated section of the gas turbine relative to a frame number is depicted.

A test of the system 42 was performed to confirm detection of peak pixel intensities corresponding to trailing edges 72 of the blades 30 and changes in a spacing of peak pixel intensities due to locked blade assemblies 20. In a test setup, a fourth row 76 of blade assemblies 20 was used in which two consecutive blade assemblies 20 were intentionally locked. In addition, a camera 44 having a frame rate of approximately 120 frames per second was used to capture images of the illuminated section 68 during rotation of the blades 30 about the center axis 17. FIG. 9 is a graph 100 of test results in which a pixel intensity 102 of light reflected from the illuminated section 68 relative to a frame number 104 is depicted. The graph 100 depicts a plurality of peak pixel intensities 106-134. As previously described, an amount of light reflected from the trailing edge 72 of a blade 30 in the fourth row 76 is substantially greater than an amount of light reflected from other portions of the blade 30 and the blades 30 in the adjacent row 80. Therefore, each peak intensity 106-134 corresponds to a trailing edge 72 of each blade 30. The inventors herein have confirmed correspondence of the peak intensities 106-134 with the trailing edges 72 of the blades 30 in the fourth row 76.

Referring to FIG. 9, each peak intensity 106-134 is spaced from an adjacent peak intensity by a plurality of frames, or frame counts 136. In particular, the frame counts 136 range between 61 to 71 frames. Therefore, each frame count 136 is indicative of a distance between trailing edges 72 of adjacent blades 30. For example, peak 108 is separated from preceding peak 106 by a frame count 136 of 66 frames as shown in FIG. 9. During the test, it was determined that frame counts 136 that range between 61 and 66 frames indicate that consecutive blades 30 are evenly spaced, i.e. the blades 30 are separated by the first distance 62 and thus are not locked. It is understood that locations on each blade 30 other than the trailing edge 72 may be used by the system 42 to determine spacing between consecutive blades 30.

As previously described, a locked blade assembly 20 results in an increase in the distance between trailing edges 72 of consecutive locked blades 30. In particular, the distance is increased to a distance greater than the first distance 62. Therefore, a substantial increase in at least one frame count 136 between any of the peak intensities 106-134 relative to other frame counts 136 indicates that a distance between consecutive blades 30 has increased beyond the first distance 62. This in turn indicates that a blade assembly pair 20 has undesirably locked. Referring to FIG. 9, peak 120 is separated from previous peak 118 by a frame count of 71 frames. This constitutes a substantial increase in frame counts 136 relative to the other frame counts 136 in FIG. 9 when using a camera having a frame rate of approximately 120 frames per second. This in turn indicates that a distance between consecutive blades 30 has increased beyond the first distance 62 and that a blade assembly pair 20 has undesirably locked. The inventors herein have confirmed the 71 frame count corresponds to the known locked blade assembly 20 of the test setup.

It is understood that the graph 100 may include more than one frame count 136 for peak intensities 106-134 that is substantially larger than the remaining frame counts 136, therefore indicating more than one locked blade assembly 20. Further, the graph 100 may depict at least one frame count 136 that is smaller than the remaining frame counts 136, thus indicating a decrease in the distance between consecutive blades 30 such as between an unlocked blade 30 and an adjacent locked blade 30. In an embodiment, a baseline dataset is first obtained for a row of blades 30 that does not have locked blade assemblies 20. A locked blade assembly dataset is then obtained for a row of blades 30 that has at least one locked blade assembly pair 20. The baseline dataset is then subtracted from the locked blade assembly dataset to indicate the existence of at least one locked blade assembly 20 to an operator.

Aspects of the current invention may be used during a turning gear operation in order to indicate that a seal pin 32, 34 has become wedged between a pair of blade assemblies 20. A visual inspection of the turning blade assemblies 20 may then be conducted. This significantly reduces inspection time relative to the current process that is being used. In addition, the system 42 may be installed at a customer site at minimal cost.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. An optical measurement system for detecting at least one locked blade assembly that becomes locked during a turning gear operation for a gas turbine wherein the gas turbine includes a plurality of blade assemblies arranged in rows about a center axis wherein each blade assembly includes a blade and wherein adjacent blades in a row are separated by a first distance forming a space between adjacent blades to orient each blade in a first position, comprising:
   at least one light source for emitting light that impinges on a blade surface of each blade in a row of blades;
   at least one video device for capturing images of the blades as the blades rotate about the center axis; and
   a controller for controlling operation of the light source and video device wherein the controller detects a pixel intensity associated with each blade surface and a spacing between each pixel intensity wherein the first distance is measured from a first blade that is not deflected from the first position during the turning gear operation and a change in spacing between consecutive pixel intensities indicates that a distance between the first blade and an adjacent blade has changed relative to the first distance thereby indicating at least one locked blade assembly.

2. The system according to claim 1, wherein the change in spacing includes an increase in spacing between pixel intensities.

3. The system according to claim 1, wherein the change in spacing includes a decrease in spacing between pixel intensities.

4. The system according to claim 1, wherein each detected pixel intensity is a peak pixel intensity.

5. The system according to claim 4, wherein each peak pixel intensity corresponds to a trailing edge of a blade.

6. The system according to claim 1, wherein the gas turbine includes light and video ports and the light source and video device are attached to the light and video ports, respectively.

7. The system according to claim 6, wherein the light and video ports are located on an outer diffuser of the gas turbine.

8. The system according to claim 7, wherein the light port is oriented such that the light impinges on a row of blades located adjacent an exhaust cylinder section of the gas turbine.

9. A method for detecting at least one locked blade assembly that becomes locked during a turning gear operation for a gas turbine wherein the gas turbine includes a plurality of blade assemblies arranged in rows about a center axis wherein each blade assembly includes a blade and wherein adjacent blades in a row are separated by a first distance forming a space between adjacent blades to orient each blade in a first position, comprising:
   emitting light that impinges on a blade surface of each blade in a row of blades;
   imaging the blades as the blades rotate about the center axis; and
   detecting a pixel intensity for each blade surface and a spacing between each pixel intensity wherein the first distance is measured from a first blade that is not deflected from the first position during the turning gear operation and a change in spacing between consecutive pixel intensities relative to other pixel intensities indicates that a distance between the first blade and an adjacent blade has changed relative to the first distance thereby indicating at least one locked blade assembly.

10. The method according to claim 9, wherein the change in spacing includes an increase in spacing between pixel intensities.

11. The method according to claim 9, wherein the change in spacing includes a decrease in spacing between pixel intensities.

12. The method according to claim 9, wherein each detected pixel intensity is a peak pixel intensity.

13. The method according to claim 12, wherein each peak pixel intensity corresponds to a trailing edge of a blade.

14. The method according to claim 9, wherein the gas turbine includes light and video ports and the light source and video device are attached to the light and video ports, respectively.

15. The method according to claim 14, further including orienting the light port such that the light impinges on a row of blades located adjacent an exhaust cylinder section of the gas turbine.

16. A method for detecting at least one locked blade assembly that becomes locked during a turning gear operation for a gas turbine wherein the gas turbine includes a plurality of blade assemblies arranged in rows about a center axis wherein each blade assembly includes a blade and wherein adjacent blades in a row are separated by a first distance forming a space between adjacent blades to orient each blade in a first position, comprising:

emitting light that impinges on a blade surface of each blade in a row of blades located adjacent an exhaust cylinder section of the gas turbine;

imaging the blades as the blades rotate about the center axis; and detecting a peak pixel intensity for each blade surface and a frame count indicating a spacing between peak pixel intensities wherein the first distance is measured from a first blade that is not deflected from the first position during the turning gear operation and a substantial change in a frame count between consecutive peak pixel intensities relative to other peak pixel intensities indicates that a distance between the first blade and an adjacent blade has changed relative to the first distance thereby indicating at least one locked blade assembly.

17. The method according to claim 16, wherein the change in the frame count includes an increase in the frame count between pixel intensities.

18. The method according to claim 16, wherein the change in the frame count includes a decrease in the frame count between pixel intensities.

19. The method according to claim 16, wherein a substantial change in frame count includes an increase in the frame count to 71 frames.

20. The method according to claim 16, wherein each peak pixel intensity corresponds to a trailing edge of a blade.

* * * * *